United States Patent [19]

Ulrich et al.

[11] 4,328,227
[45] May 4, 1982

[54] NOVEL O-PROPYLOXIMES

[75] Inventors: Gebert Ulrich, Kelkheim; Werner Thorwart, Wiesbaden; Jaromir Komarek, Wiesbaden; Carl Cartheuser, Wiesbaden; Kurt Popendiker, Wiesbaden; Heinz-Günther Greve, Frankfurt am Main, all of Fed. Rep. of Germany

[73] Assignee: Hoechst Aktiengesellschaft, Frankfurt am Main, Fed. Rep. of Germany

[21] Appl. No.: 150,705

[22] Filed: May 19, 1980

Related U.S. Application Data

[63] Continuation of Ser. No. 864,008, Dec. 23, 1977.

[30] Foreign Application Priority Data

Dec. 24, 1976 [DE] Fed. Rep. of Germany ...... 2658938

[51] Int. Cl.³ .............. A61K 31/495; C07D 401/12; C07D 405/12; C07D 403/12
[52] U.S. Cl. .................................. 424/250; 542/416; 544/360; 544/368; 544/370; 544/371; 544/373; 544/376; 544/379; 544/272; 546/192; 546/195; 424/267; 424/251
[58] Field of Search ............... 544/360, 370, 371, 368, 544/373, 376, 379; 424/250; 564/256, 257; 542/416

[56] References Cited

U.S. PATENT DOCUMENTS

| | | | |
|---|---|---|---|
| 2,712,031 | 6/1955 | Huffman | 564/256 |
| 2,832,804 | 4/1958 | Richter et al. | 564/257 |
| 3,060,177 | 10/1962 | Druey et al. | 544/371 |
| 3,692,835 | 9/1972 | Van Dijk et al. | 564/256 |
| 3,903,164 | 9/1975 | Göransson-Dahlander | 544/165 |
| 3,904,689 | 9/1975 | Ashby | 564/256 |
| 3,951,983 | 4/1976 | Danilewicz et al. | 424/250 |
| 3,951,986 | 4/1976 | Maruyama et al. | |
| 3,953,449 | 4/1976 | Guidicelli et al. | 544/360 |
| 3,954,763 | 5/1976 | Giudicelli et al. | 424/250 |
| 3,960,956 | 6/1976 | Uyeda | |
| 4,038,317 | 7/1977 | Wermuth et al. | 564/257 |
| 4,100,282 | 7/1978 | Renth et al. | 544/360 |
| 4,187,220 | 2/1980 | Takacs et al. | 564/256 |
| 4,207,319 | 6/1980 | Thuillier et al. | 544/379 |

OTHER PUBLICATIONS

Burger, Medicinal Chemistry, vol. 1, pp. 27–50, (1951).

Primary Examiner—Donald G. Daus
Assistant Examiner—Sharon A. Gibson
Attorney, Agent, or Firm—Quaintance & Murphy

[57] ABSTRACT

Compounds of general formula

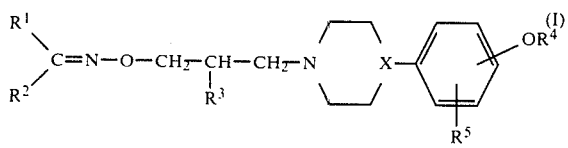

wherein $R^1$ represents a radical selected from the group consisting of
(a) hydrogen, carboxyl;
(b) alkyl, alkenyl each having up to 6 carbon atoms and their phenyl substituted derivatives;
(c) at most binuclear unsubstituted aryl, at most binuclear aryl substituted by from 1 to 3 substituents selected from the group consisting of alkyl and alkoxy each having up to 6 carbon atoms, benzloxy, haloalkyl having up to 2 carbon atoms, halogen, cyano and nitro; amino, carboxyl and hydroxy; amino, carboxyl and hydroxy each being substituted by alkyl having at most 2 carbon atoms, methylenedioxy groups and O-<3-[4-(2-methoxyphenyl)-1-piperazinyl]-2-hydroxypropyl>-hydroximinomethyl groups;
(d) at most bicyclic unsubstituted heteroaromatic group having 1 to 4 heteroatoms selected from the group consisting of nitrogen, one sulphur and one oxygen in the ring system and such a heteroaromatic group being substituted by at most 3 substituents selected from the group consisting of alkyl, alkoxy each having up to 2 carbon atoms, phenylalkyl having up to 3 carbon atoms in the alkyl moiety, halogen, methylamino and dimethylamino;

$R^2$ represents a member selected from the group consisting of hydrogen, alkyl having up to 3 carbon atoms, cycloalkyl having up to 6 carbon atoms and phenyl; and $R^1$ and $R^2$, together with the carbon atom to which they are attached, form a radical selected from the group consisting of fluorene-9-ylidene and a cycloaliphatic group having up to 10 carbon atoms and such a cycloaliphatic group containing a hydrocarbon bridging group;

$R^3$ represents a member selected from the group consisting of hydrogen hydroxy and acyloxy;

$R^4$ represents a member selected from the group consisting of hydrogen alkyl having up to 3 carbon atoms and phenyl;

$R^5$ represents a member selected from the group consisting of halogen, alkoxy having up to 2 carbon atoms and hydroxy; and X represents a member selected from the group consisting of nitrogen and methine and physiologically acceptable acid addition salts thereof; a pharmaceutical composition containing said compounds.

6 Claims, 1 Drawing Figure

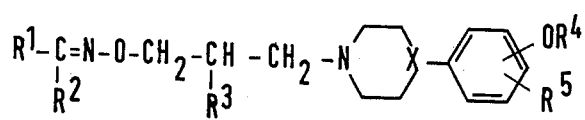 
(I) (II)
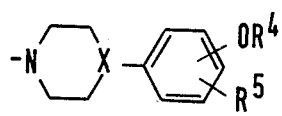 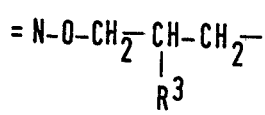 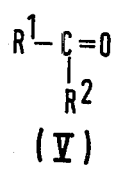
(III) (IV) (V)
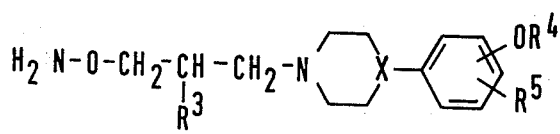 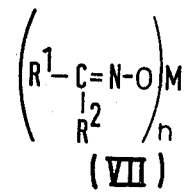
(VI) (VII)
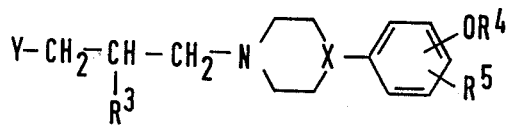 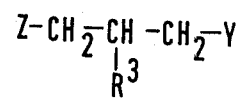
(VIII) (IX)
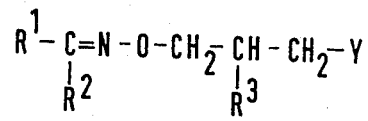 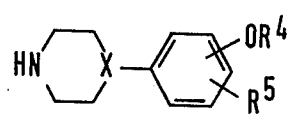
(X)
(XI)

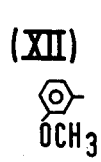  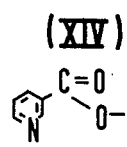 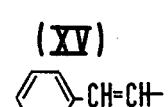 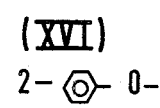
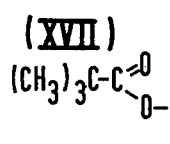 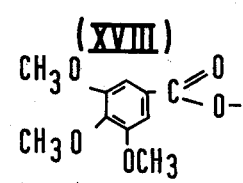 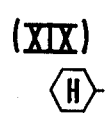 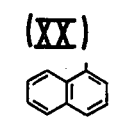 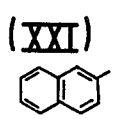
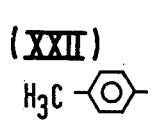 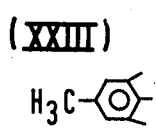 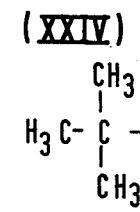 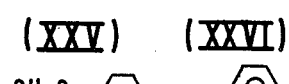 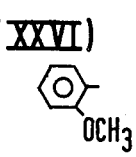
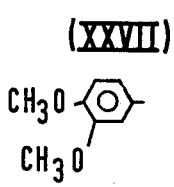 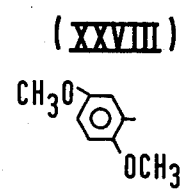 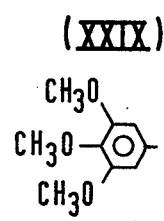 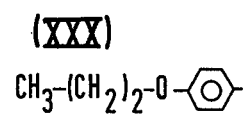
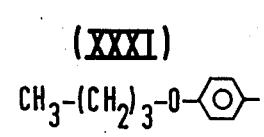 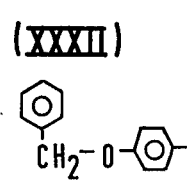 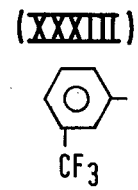 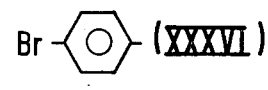 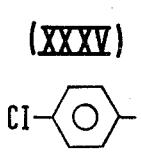
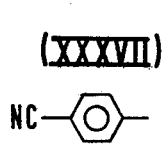 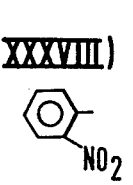 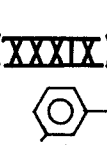 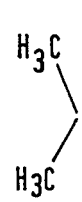 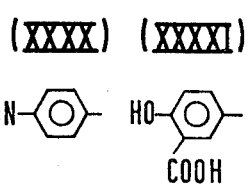 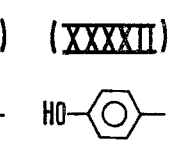
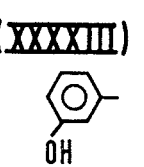 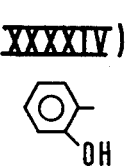 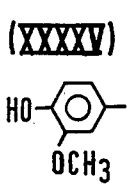 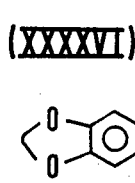 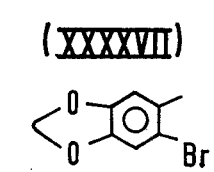

NOVEL O-PROPYLOXIMES

This is a continuation of copending application Ser. No. 864,008 filed Dec. 23, 1977.

This invention relates to novel substituted O-propyloximes having interesting pharmacological properties.

Research has hitherto been directed towards obtaining pharmacologically active compounds having theraputic benefits by reacting salicylic acid aldehydes with O-[2-(4-morpholinyl)-ethyl]-hydroxylamine, oximes with diethylamino-, morpholino-, pyrrolidino- and 4-methylpiperazino-alkyl halides and by reacting O-(2,3-epoxypropyl)-oximes with ammonia, dimethyl-, diethyl-; n-propyl- isopropyl- and tert.-butyl-amine.

We have now surprisingly found that pharmacologically active compounds may be obtained by introducing a 4-phenylpiperazinyl or 4-phenylpiperidinyl group having at least one substituent containing oxygen in the phenyl group into the side chain of O-propylated oximes. We have found that these derivatives exhibit a useful activity on the cardiovascular system.

Thus, according to one aspect of the present invention there are provided compounds of general formula

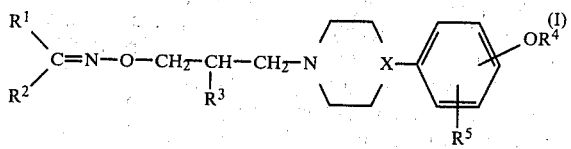
(I)

(wherein $R^1$ represents
(a) a hydrogen atom of a carboxyl group;
(b) an alkyl or alkenyl group each having up to 6 carbon atoms and optionally substituted by a phenyl group;
(c) a mono- or binuclear aryl group optionally substituted by from 1 to 3 substituents selected from alkyl or alkoxy groups each having up to 6 carbon atoms, benzyloxy groups, haloalkyl groups having up to 2 carbon atoms, halogen atoms, cyano or nitro groups, amino, carboxyl or hydroxy groups each of the last three groups substituted by methyl and/or ethyl groups; methylenedioxy groups and O-{3-[4-(2-methoxyphenyl)-1-piperazinyl]-2-hydroxypropyl}-hydroximinomethyl groups;
(d) a mono- or bicyclic heteroaromatic group having from 1 to 4 nitrogen atoms or a sulphur or oxygen atom in the ring system and being optionally substituted by at most 3 substituents selected from alkyl or alkoxy groups each having up to 2 carbon atoms, phenylalkyl groups having up to 3 carbon atoms in the alkyl moiety, halogen atoms, methylamino and dimethylamino groups;
$R^2$ represents a hydrogen atom or an alkyl group having up to 3 carbon atoms, a cycloalkyl group having up to 6 carbon atoms or a phenyl group; or $R^1$ and $R^2$, together with the carbon atom to which they are attached, form a fluorene-9-ylidene group or a cycloaliphatic group having up to 10 carbon atoms optionally containing a hydrocarbon bridging group; $R^3$ represents a hydrogen atom or a hydroxy or acyloxy group; $R^4$ represents a hydrogen atom of an alkyl group having up to 3 carbon atoms or a phenyl group; $R^5$ represents a hydrogen or halogen atom or an alkoxy group having up to 2 carbon atoms or a hydroxy group; and X represents a nitrogen atom or a methine group) and physiologically acceptable acid addition salts thereof.

When $R^3$ in the compounds of formula I represents an acyloxy group, the acyl moiety thereof is preferably derived from a straight-chained or branched alkane carboxylic acid having up to 6 carbon atoms and most preferably is derived from nicotinic acid or benzoic acid optionally substituted up to 3 times with alkoxy groups having from 1 to 4 carbon atoms.

Compounds of formula I and the physiologically acceptable acid addition salts thereof exhibit interesting pharmacological properties and in particular hypotensive properties together with good compatibility and may therefore be useful in the treatment of hypertonia.

Preferred compounds of formula I are those in which $R^2$ is hydrogen. Of these compounds especially preferred are those in which $R^1$ represents an optionally substituted phenyl, pyridyl or imidazolyl group;
$R^3$ represents a hydrogen atom or a hydroxyl group;
$OR^4$ represents a hydroxy, methoxy or ethoxy group in the 2- or 4-position of the phenyl ring;
$R^5$ represents a hydrogen atom; and
X represents a nitrogen atom.

The compounds according to the invention may be prepared by linking compounds having a group

(II)

with compounds having a group

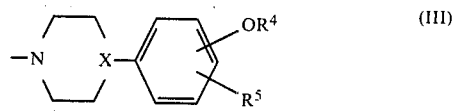
(III)

via the group

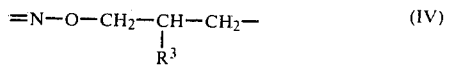
(IV)

(in which $R^1$, $R^2$, $R^3$, $R^4$, $R^5$ and X are as hereinbefore defined).

Thus, compounds of general formula I may be prepared by the following processes, which processes constitute further features of the present invention:

(A) reacting a carbonyl compound of formula

(V)

(in which $R^1$ and $R^2$ are as hereinbefore defined) or a reactive derivative thereof with a hydroxylamine derivative, of formula

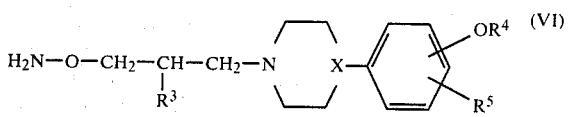
(VI)

(in which $R^3$, $R^4$, $R^5$ and X are as hereinbefore defined) or a salt thereof;

(B) reacting an oxime of formula

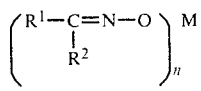 (VII)

(in which R$^1$ and R$^2$ are as hereinbefore defined, M represents a hydrogen atom or an alkali metal or alkaline earth metal cation, and n represents the integer 1 when M represents a hydrogen atom, or the valency of the cation when M represents an alkali metal or alkaline earth metal cation) with (B1) a substituted propyl compound of formula

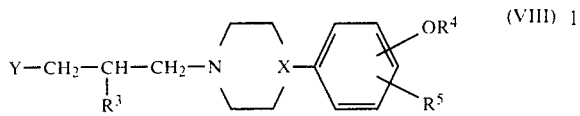 (VIII)

(in which R$^3$, R$^4$, R$^5$ and X are as hereinbefore defined and Y represents a halogen, preferably a chlorine or bromine, atom, or a reactive sulphonic acid ester group, or Y and R$^3$, together with the two carbon atoms to which they are attached, form an oxirane ring) or a salt thereof, or (B2) a propyl derivative of formula

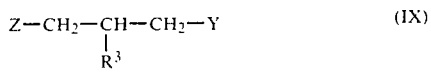 (IX)

(wherein R$^3$ and Y are as hereinbefore defined and Z represents a halogen, preferably a chlorine or bromine, atom or a reactive sulphonic acid ester group) to form an O-alkylated oxime of formula

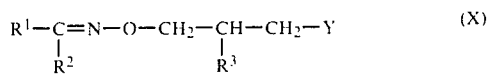 (X)

(in which R$^1$, R$^2$, R$^3$ and Y are as hereinbefore defined) which is subsequently reacted with an amine of formula

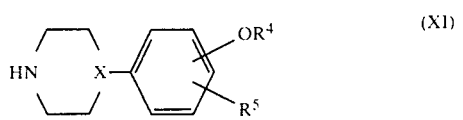 (XI)

(in which R$^4$, R$^5$ and X are as hereinbefore defined); or (C) acylating a compound of formula I in which R$^3$ represents a hydroxy group.

Acylation of the compounds according to the invention, in which R$^3$ represents a hydroxyl group, may be effected with carboxylic acids preferably in the presence of condensation agents such as for example carbodiimides. It is preferred however to effect the acylation using reactive functional derivatives of the acids, such as for example, acid halides, anhydrides or reactive esters.

Examples of carbonyl compounds of formula V which may be used in process A) are, for example, aldehydes such as acetic, isobutyric, crotonic and cinnamic aldehyde; glyoxylic acid; benzaldehyde and variously substituted derivatives thereof such as 4-methyl-, 2,4,6-trimethyl-, 4-tert.-butyl-, 2-,3-, or 4-methoxy-, 3,4- or 2,5-dimethoxy-,3,4,5-trimethoxy-,4-propoxy-,4-butoxy-,3-trifluoromethyl-,4-fluoro-, 4-chloro-,4-bromo-,4-cyano-,2-, or 3-nitro-,4-dimethylamino-, 2-,3- or 4-hydroxy-,4-hydroxy-3-methoxy-,3,4-methylenedioxy or 2-bromo-4,5-methylenedioxy-benzaldehyde; terephthaldehyde; 5-formylsalicyclic acid and α-or β-naphthaldehyde; and ketones such as for example acetophenone, 4-chloroacetophenone, benzophenone, cyclohexylphenylketone and 4-benzyloxypropiophenone.

Examples of heteroaromatic carbonyl compounds of formula V are, among others, the three isomeric formyl- or benzoylpyridines, 3-indolaldehyde and its 5-methoxy derivative, 5-chloro- or 5-dimethylamino-1,3-dimethyl-4-benzoylpyrazole, 1,3-dimethyl-4-methylamino-5-benzoylpyrazole, 1-methyl- or 1-(1-phenylethyl)-imidazole-2-carbaldehyde, 8-formylcaffeinethiophene-2and chromono-3-carbaldehyde.

Cyclic ketones of formula V such as, for example, cyclohexanone, camphor, adamantan-2-one and fluorenone, may also if desired be used.

Carbonyl compounds for use in process A may also be in the form of their reactive derivatives such as for example hemi- or full acetals, mercaptals, aminals or acylals. Also, aldimines, oximes (such as of formula VII), hydrazones, semicarbazones, thiosemicarbazones, cyanohydrins of bisulfite addition compounds may be used as starting compounds of formula V in process A).

Examples of compounds of formula VI for use in process A) are substituted O-propyl-hydroxylamines known from the literature or easily prepared by processes known in the literature. The latter compounds may be substituted in the three position of the propyl group by, for example, a 4-(2- or 4-hydroxyphenyl)-, 4-(2,4-dihydroxyphenyl)-, 4-(2-, 3- or 4-methoxyphenyl)-, 4-(2,4-or 3,5-dimethoxyphenyl)-, 4-(2-ethoxyphenyl)-, 4-(2-phenoxyphenyl)- or 4-(4-chloro-2-methoxyphenyl)-1-piperazinyl- or -1-piperidyl- group.

Oximes of formula VII for use in process B are known or can easily be prepared by methods known from the literature e.g. by reacting aldehydes or ketones of formula V with hydroxylamine and optionally subsequent salt formation.

Starting compounds of formula VIII are, for example, 1-(-3-halogenopropyl)-, 1-(3-halogeno-2-hydroxypropyl)- and 1-(2,3-epoxypropyl)-piperazines and -piperidines arylated in the 4-position analogously to compounds of formula VI.

Examples of epoxides of formula IX for the conversion of oximes of formula VII into intermediate of formula X (in which R$^3$ and Y together with the two carbon atoms to which they are attached form an oxirane ring) are, for example, epibromohydrin, 2,3-epoxypropyl-benzene sulphonate, -p-toluene sulphonate,- methane sulphonate and conveniently epichlorohydrin. Other examples of compounds of formula IX are 1,3-dihalogeno-2-propanols such as 1,3-dichloro-, 1,3-dibromo- and 1-bromo-3-chloro-2-propanol.

Intermediates of formula X in which R$^3$ represents a hydrogen atom may be preferably prepared using 3-halogenopropyl sulphonates or 1,3-dihalogeno-propanes of formula IX, and especially 1-bromo-3-chloropropane.

Amines of formula XI which may be used in process B2 are, for example, 4-(2- or 4-hydroxy-phenyl)-, 4-(2,4-dihydroxy-phenyl)-, 4-(2-,3- or 4-methoxyphenyl)-, 4-(2,4- or 3,5-dimethoxyphenyl)-, 4-(2-ethoxyphenyl)-, 4-(2-phenoxy-phenyl)-, and 4-(4-chloro-2-methoxyphenyl) -piperidine or piperazine.

The processes according to the invention may if desired, be carried out in a solvent or dispersion agent.

Process A is preferably effected using equimolar quantities of the starting materials in an aqueous-alcoholic solvent. However, it is also possible to use other solvents which are inert under the reaction conditions, such as, for example, pyridine, dimethylformamide and alcohols e.g. methanol, ethanol, the various propanols and butanols or mixtures of these solvents. The hydroxylamine derivatives of formula VI are advantageously used in the form of their acid addition salts such as hydrochlorides, hydrobromides or sulphates. In the latter case, it is preferred to add to the reaction mixture at least a stoichiometric quantity of an acid-binding agent, such as for example, an alkali metal or alkaline earth metal hydroxide or carbonate or an organic base such as triethylamine. This condensation reaction of process A is preferably carried out at a temperature of from 0° C. to the boiling point of the reaction mixture, conveniently between 50° and 100° C., and most preferably between 50° and 80° C., the reaction time ranges from a few minutes to a few hours.

Alkylation of oximes of formula VII with compounds of formula VIII or IX according to process B can be carried out, for example, in anhydrous alcohols, hydrocarbons, aprotic solvents and also an excess of the alkylating agent of formula VIII or IX used. It is preferred to effect the alkylation reaction of the oximes in the presence of a base such as, for example, an alkali metal or alkaline-earth metal hydroxide, carbonate, hydride or alcoholate or in an organic base (e.g. triethylamine, pyridine, picoline or quinoline) or alternatively alkali metal or alkaline-earth metal oximates prepared separately may be used.

Alcohols for use as the solvent are, among others, methanol, ethanol, propanol, isopropanol, the various butanols, (e.g. isobutanol), and hydrocarbons for use as the solvent are, for example, hexane, cyclohexane, benzene, toluene or xylene. Examples of aprotic solvents are, for example, dimethylformamide, dimethylacetamide, N-methyl-pyrrolidone, tetramethyl urea, hexamethyl phosphoric acid trisamide and dimethylsulphoxide. Depending on the particular process, reaction temperatures are generally between 0° C. and the boiling point of the reaction mixture. However, a temperature above 20° C. is preferably employed. When working in an alcoholic medium temperatures are from preferably 50° to 100° C. and in aprotic solvents from 80° to 120° C., e.g. about 100° C. The reaction times are generally between 1 and 10 hours.

Reaction of the intermediate of formula X in which Y represents a halogen atom or a reactive sulphonic acid ester group with the amines of formula XI in process B2 is preferably effected under the same conditions as in the first stage. Aminolysis of O-(2,3-epoxypropyl)-oximes of formula X (in which $R^3$ and Y together represent oxygen) with the amines of formula XI preferably takes place, however, by heating for 1 to 5 hours in higher-boiling alcohols such as n-propanol, isopropanol, n-butanol or isobutanol in the absence of other bases, the starting materials preferably being used in equimolar quantities.

When in any of the above processes, the products of formula I are obtained in the form of their free bases, these may if desired be converted into the corresponding physiologically acceptable acid addition salts in known manner. Similarly when acid addition salts of the products are obtained, these may if desired be converted to the corresponding free bases of formula I.

Suitable acids for producing physiologically acceptable acid addition salts of the compounds of formula I according to the invention are, for example, halogen hydracids, especially hydrochloric acid, sulphuric acid, phosphoric acid, and organic acids such as, for example, acetic acid, lactic acid, maleic acid, fumaric acid, oxalic acid, tartaric acid, citric acid, gluconic acid, p-toluenesulphonic acid, methanesulphonic acid and cyclohexylamidosulphonic acid. It will be appreciated that compounds of formula I according to the invention may occur in the form of E and/or Z stereoisomers on the basis of known oxime isomerism. It will also be appreciated that if $R^3$ represents a hydroxy or acyloxy group the compounds additionally possess a chiral carbon atom and may thus exist in the optically active D and/or L forms as well as racemates thereof. All such forms of the compounds are intended to be within the scope of the invention.

Pure antipodes of the compounds of formula I may be produced by effecting the reactions according to processes A, B and C starting from the enantiomeric starting compounds of formula VI or VIII and IX or alternatively by resolving racemates of the products into the enantiomers thereof by known processes, e.g. by fractional crystallisation of the diastereomeric acid addition salts formed with an optically active acid.

As indicated above the novel oximes of formula I and the physiologically acceptable salts thereof possess interesting pharmacological properties, and in particular may be useful in the treatment of hypertonic conditions.

According to a further aspect of the present invention there is provided a pharmaceutical composition comprising as active ingredient at least one compound of formula I or a physiologically acceptable acid addition salt thereof in association with a pharmaceutical carrier or excipient.

The compositions according to the inventions are preferably in a form suitable for oral, rectal or parenteral administration, such forms being for example tablets coated tablets, capsules, solutions, suspensions, drops, emulsions, granulates, powders, syrups, suppositories, injectable solutions and forms adapted to provide a sustained release of active ingredient. These forms may be formulated using pharmaceutical carriers or excipients conventionally used in the pharmaceutical art.

It is, however, possible to administer the compounds according to the invention in the absence of carriers or excipients, for example in the form of microcapsules.

If desired, the composition according to the invention can be administered in the form of dosage units.

Suitable dosages for human oral administration are for example, 1 to 10, preferably 3 to 5 mg/day. In animals a convenient single dose is for example 0.1 to 10, preferably 0.3 to 3 mg/kg i.v.

Carriers which may be used in the compositions are for example, magnesium carbonate, various sugars, starch, cellulose derivatives, gelatin, animal and vegetable oils, polyethylene glycols and solvents.

The compositions according to the invention may, if desired, additionally comprise one or more further pharmacologically active ingredients such as, for example, diuretics, saluretics, $\alpha$- and especially $\beta$- sympatholytics, tranquillizers, vasodilating agents and other antihypertensives.

Pharmacological tests and results

Our tests have shown that compounds of formula I according to the invention and the physiologically acceptable said addition salts thereof have a hypotensive activity on anesthetised normotonic dogs and an anti-hypertensive activity on high blood-pressure animals (dogs and rats).

1. Hypotensive Activity

The test animals used were bastard dogs of both sexes under sodium pentobarbital anaesthetia (35–40 mg/kg i.p.), which during the test lay on an operating table heated to 37° C. and the animals were allowed to breathe spontaneously through a tracheal tube. To prevent blood coagulation they were administered 2 mg/kg of heparin i.v.

The substances to be tested were administered
 (a) intravenously (i.v.) in aqueous solution through a polyvinyl chloride catheter into the femoral vein. The administration time was in each case 30 seconds.
 (b) intraduodenally (i.d.) in the form of carboxymethylcellulose suspensions through a polyvinylchloride catheter into the duodenum.

The following cardio-vascular measurements were made:
 1. p = average arterial blood pressure in mm Hg through a polyvinyl chloride catheter by a Statham electronic pressure recorder.
 2. Heart frequency (min$^{-1}$) by a ECG (2nd extremity lead) by counting the R serrations.
 3. dp/dt$_{max}$ (mmHg. sec$^{-1}$) by a differentiator.

The most important test results are set out in Table 1, in which n represents the number of test animals.

2. Anti-hypotensive Activity

(a) Genetic High-blood-pressure rats

The test animals used were live genetic high blood-pressure rats (Wistar SH) obtained from Buckshire Corp./Perkasie, Pennsylvania, U.S.A. Groups of 5 to 6 animals were administered the test substances per os on the morning of 3 consecutive days. Blood pressure was measured 2, 4, 6 and 24 hours after administration of the compounds by piezoelectric pulse microphones attached to the animals' tails, the pulses being transmitted via an amplifier system to a Hellige 6-channel pen recorder.

These tests show that compounds according to the invention have a strong hypotensive effect with doses of 7.5 mg/kg per os and this effect lasts longer than 6 hours. Table 2 indicates the maximum drop in blood pressure against the initial value on the first test day, in the Table n represents the number of test animals.

(b) Renal high-blood pressure dogs

The substances were tested over several days on a group of live, trained, pure-bred beagle dogs (n≧5) having a stable renal high blood pressure (aseptic perinephritis by investing both kidneys with a cellular glass foil). Blood pressure measurements were carried out on the tail artery according to the conventional Riva-Rocchi method. Each morning after the first blood pressure measurement (initial value) the animals were given the appropriate test substance in gelatine capsules per os in the specified dose (active dose W). Further blood pressure measurements were made 1½, 3, 5 and 7 hours after administration of the preparation. The animals were then given a second dose of the test substance (maintaining dose E). The average blood pressure values of all animals for the same test times were checked by means of the t test according to Student against the initial value for the significance (= probability of error). The results are set out in Table 3.

In comparison with the commercial anti-hypotensive product, prazosin [1-(4-amino-6,7-dimethoxy-2-quinazolinyl)-4-(2-furoyl)-piperazine hydrochloride], the hypotensive activity of which is accompanied by an undesirable tachycardia, the compounds according to the invention generally show a bradycardiac action and thus relieve the heart. The pressor reaction on catecholamines supplied exogenically is only moderately inhibited by them whereas the comparison product causes complete blockage of the α-receptors resulting in a reversal of the adrenalin reaction.

It has been demonstrated that the compounds of the present invention have only a slight α-sympathicolytic activity on the isolated seminal vesicle of the guinea pig, whereas prazosin has a strong α-sympathicolytic activity comparable to phentolamine.

A further advantage over the comparison preparation prazosin is that the compounds according to the invention show anti-hypertensive activity with a preferably central activity mechanism.

The following Examples serve to illustrate the preparation of compounds according to the invention. The structure of the compounds described was proved by elemental analysis and by i.r. and $^1$H-n.m.r spectra.

EXAMPLE 1

O-<3-[4-(2-Methoxyphenyl)-1-piperazinyl]-2-hydroxypropyl>-3-methoxy-benzaldoxime dihydrochloride (See Table 4 for formula)
(According to process A)

20.4 g (0.15 mol) of 3-methoxybenzaldehyde are dissolved in 400 ml of ethanol. After the addition of 61.3 g (0.15 mol) of O-<3-[4-(2-methoxyphenyl)-1-piperazinyl]-2-hydroxypropyl>-hydroxylamine trihydrochloride monohydrate in 150 ml of water, a solution of 23.9 g (0.225 mol) sodium carbonate in 125 ml of water is added dropwise with continuous stirring at room temperature. The mixture is then stirred for 30 minutes at room temperature and subsequently for 1 hour at 60°–70° C. The ethanol is then distilled off under reduced pressure, the residue mixed with ethyl acetate and the sodium chloride is removed by washing several times with water. After drying over sodium sulphate and evaporation under reduced pressure, the organic phase yields crude base (100%) which is converted into the dihydrochloride by dissolving in dry ethyl acetate and mixing dropwise with 0.3 mol of ethanolic hydrochloric acid with stirring and cooling. The product precipitated is filtered off, washed with diethyl ether and optionally recrystallized from ethanol with the addition of diethyl ether at boiling heat until turbidity.

Yield: 61.5 g (86.8% of theory); melting point 171°–173° C.; $C_{22}H_{31}Cl_2N_3O_4$ (mw. = 472.4)

Analysis:
Calculated. C 55.93%; H 6.61%; Cl 15.01%; N 8.89%; Found: C 55.88%; H 6.62%; Cl 15.09%; N 8.99%.

EXAMPLE 2

O-<3-[4-(2-Methoxyphenyl)-1-piperazinyl]-2-hydroxypropyl>-benzaldoxime hydrochloride (See Table 4 for formula)

(According to process B2)

To a solution of 5.75 g (0.25 gram atom) of sodium in 250 ml of anhydrous ethanol is added 30.3 g (0.25 mol) of benzaldoxime, the mixture is stirred for 30 minutes at room temperature and the alcohol is removed under reduced pressure.

The dried sodium oximate is added in portions over 30 minutes with stirring at 80° C. to 156 ml (2 mol) of epichlorohydrin and the mixture is kept at this temperature for a further 5 hours. After cooling, the solution is filtered off from precipitated sodium chloride and excess epichlorhydrin is distilled off under reduced pressure. Fractional distillation of the oily residue in vacuo gives 29.2 g (65.9% of theory) of O-(2,3-epoxypropyl)-benzaldoxime of boiling point (0.3 torr) 121°–124° C. 26.6 g (0.15 mol) of this epoxide are dissolved, together with 28.8 g (0.15 mol) of 1-(2-methoxyphenyl)-piperazine, in 100 ml of isopropanol and refluxed for 4 hours. On addition of a stoichiometric quantity of ethanolic hydrochloric acid to the cooled reaction mixture the monohydrochloride is formed, which is recrystallised from ethanol with the addition of diethyl ether at boiling heat until turbidity.

Yield:
45.1 g (74% of theory); melting point 163°–164° C.;
$C_{21}H_{28}ClN_3O_3$ (m.w. = 405.9)
Analysis:
Calculated: C 62.14%; H 6.70%; Cl 8.98%; N 10.35%; Found: C 61.81%; H 6.98%; Cl 8.66%; N 10.03%.

The base of the above hydrochloride also forms crystalline oxalate and cyclamate salts with melting points of 143°–144° C. and 90°–91° C. respectively.

EXAMPLE 3

O-<3-[4-(2-Methoxyphenyl)-1-piperidyl]-2-hydroxypropyl)benzaldoxime hydrochloride (See Table 4 for formula)

(According to process B2)

5.3 g (0.03 mol) of the O-(2,3-epoxypropyl)-benzaldoxime prepared in the first stage of Example 2 and 5.7 g (0.03 mol) of 4-(2-methoxyphenyl)-piperidine are dissolved in 50 ml of isopropanol and refluxed for 4 hours. The mixture is allowed to cool, mixed with ethanolic hydrochloric acid, and the crystalline precipitation is separated and re-crystallised from ethanol.

Yield: 8.2 g (67.2% of theory); melting point 155°–157° C.;
$C_{22}H_{29}ClN_2O_3$ (m.w. = 404.9)
Analysis:
Calculated C 65.24%; H 7.24%; Cl 8.75%; N 6.92%; Found C 65.32%; H 7.04%; Cl 8.74%; N 6.77%.

EXAMPLE 4

O-<3-[4-(2-Methoxyphenyl)-1-piperazinyl]-propyl>-benzaldoxime dihydrochloride (See Table 4 for formula)

(According to process B1)

To a solution of 1.84 g (0.08 gram atom) of sodium in 150 ml of anhydrous ethanol is added 9.7 g (0.08 mol) of benzaldoxime, the mixture is stirred for 30 minutes at room temperature, and then mixed with 21.5 (0.08 mol) of 3-[4-(2-methoxyphenyl)-1-piperazinyl]-propylchloride and refluxed for 8 hours. The reaction mixture is then evaporated under reduced pressure, the residue is mixed with water and the reaction product is extracted with chloroform. After drying over sodium sulphate, the solvent is again distilled off under reduced pressure, the resulting oily residue is dissolved in dry ethyl acetate and acidified with ethanolic hydrochloride, the product being precipitated as voluminous solid substance in the form of the dihydrochloride. The yield is 22.4 g (65.3% of theory) after recrystallizing twice from isopropanol. Melting point 188°–189° C.;
$C_{21}H_{29}Cl_2N_3O_2$ (m.w. = 426.4).
Analysis:
Calculated C 59.16%; H 6.86%; Cl 16.63%; N 9.85%; Found C 58.93%; H 6.90%; Cl 16.36%; N 9.92%.

EXAMPLE 5

O-<3-[4-(2-Methoxyphenyl)-1-piperazinyl]-2-nicotinoyloxypropyl>-benzaldoxime dihydrochloride (See Table 4 for formula)

18.5 g (0.05 mol) of O-<3-[4-(2-methoxyphenyl)-1-piperazinyl]-2-hydroxypropyl>-benzaldoxime from Example 2 are dissolved according to process C in 200 ml of chloroform and after the addition of 8.5 g (0.06 mol) of nicotinic acid chloride are refluxed for 12 hours. The mixture is then allowed to cool, the chloroform solution is washed with 2 N sodium hydroxide solution and water, dried over sodium sulphate and evaporated under reduced pressure. The residue is dissolved in warm isopropanol and mixed with ethanolic hydrochloric acid, the title compound being precipitated in crystalline form. Recrystallising several times from isopropanol gives 24.5 g (89.6% of theory) of analytically pure product with melting point 188°–189° C.;
$C_{27}H_{32}Cl_2N_4O_4$ (m.w. = 547.5)
Analysis:
Calculated C 59.23%; H 5.89%; Cl 12.95%; N 10.23%; Found C 59.41%; H 6.12%; Cl 12.73%; N 10.06%.

The compounds listed in Table 4 are prepared analogously by process A, B or C:

TABLE 1

| | | Hypotensive Activity | | | |
|---|---|---|---|---|---|
| Compound of Example | Dose in, mg/kg | Administration route | n | Maximum change in mean arterial blood pressure (%) | Time taken to return to initial value (minutes) |
| 1 | 0.3 | i.v. | 3 | −12 | 10 |
| | 1 | | 4 | −18 | >48 |
| | 3 | | 5 | −38 | 99 |
| | 6 | | 2 | −47 | >70 |
| | 3 | i.d. | 3 | −22 | >113 |
| | 5 | | 3 | −38 | >120 |
| 2 | 0.3 | i.v. | 5 | −15 | 50 |
| | 1 | | 7 | −27 | >77 |
| | 3 | | 6 | −39 | >101 |
| | 10 | i.d. | 2 | −22 | 210 |
| | 20 | | 1 | −40 | >300 |
| 3 | 3 | i.v. | 2 | −29 | 90 |
| | 6 | | 2 | −33 | >90 |
| | 20 | i.d. | 2 | −31 | >180 |
| 4 | 1 | i.v. | 5 | −18 | 61 |
| | 3 | | 6 | −29 | >85 |
| | 6 | | 2 | −34 | >75 |
| | 20 | i.d. | 5 | −20 | >236 |
| 5 | 3 | i.v. | 2 | −44 | 95 |
| | 6 | | 2 | −39 | >60 |

TABLE 1-continued

Hypotensive Activity

| Compound of Example | Dose in, mg/kg | Administration route | n | Maximum change in mean arterial blood pressure (%) | Time taken to return to initial value (minutes) |
|---|---|---|---|---|---|
|  | 20 | i.d. | 5 | −24 | >64 |
| 13 | 1 | i.v. | 4 | −23 | 37 |
|  | 6 |  | 3 | −31 | 62 |
|  | 10 |  | 1 | −45 | 60 |
|  | 5 | i.d. | 7 | −15 | 68 |
|  | 10 |  | 5 | −22 | >108 |
|  | 15 |  | 2 | −40 | >120 |
| 19 | 3 | i.v. | 2 | −24 | 28 |
|  | 6 |  | 2 | −43 | 58 |
|  | 20 | i.d. | 3 | −23 | >177 |
| 30 | 3 | i.v. | 2 | −39 | 75 |
|  | 6 |  | 2 | −48 | 70 |
|  | 20 | i.d. | 2 | −28 | 115 |
| 36 | 1 | i.v. | 4 | −31 | 66 |
|  | 3 |  | 8 | −37 | 100 |
|  | 6 |  | 2 | −41 | 100 |
|  | 10 | i.d. | 3 | −33 | 178 |
| 39 | 3 | i.v. | 2 | −45 | >58 |
|  | 20 | i.d. | 2 | −31 | >155 |
| 56 | 3 | i.v. | 1 | −38 | 25 |
|  | 6 |  | 1 | −54 | >30 |
|  | 10 | i.d. | 1 | −34 | >155 |
|  | 20 |  | 2 | −47 | >90 |
| 58 | 3 | i.v. | 2 | −58 | >107 |
|  | 3 | i.d. | 2 | −9 | >53 |
|  | 10 |  | 1 | −46 | >340 |
| 62 | 3 | i.v. | 2 | −41 | >185 |
|  | 6 |  | 1 | −52 | >100 |
|  | 10 | i.d. | 2 | −34 | 280 |
| 69 | 3 | i.v. | 2 | −45 | >83 |
|  | 6 |  | 1 | −43 | 62 |
|  | 20 | i.d. | 1 | −42 | >300 |
| 75 | 3 | i.v. | 2 | −34 | >75 |
|  | 10 | i.d. | 2 | −37 | >235 |
|  | 20 |  | 3 | −44 | >313 |
| 88 | 0.3 | i.v. | 2 | −30 | 20 |
|  | 3 |  | 2 | −39 | 65 |
|  | 6 |  | 2 | −45 | 55 |
|  | 1 | i.d. | 1 | −24 | 80 |
|  | 3 |  | 5 | −26 | >160 |
|  | 6 |  | 3 | −30 | >82 |
|  | 20 |  | 2 | −37 | >150 |
| 93 | 3 | i.v. | 2 | −32 | 90 |
|  | 20 | i.d. | 4 | −22 | >170 |

TABLE 2

Anti-hypertensive activity (high blood pressure rats)

| Compound of Example | Dose in mg/kg p.o. | n | Maximum change in systolic blood pressure |
|---|---|---|---|
| 1 | 7.5 | 6 | −15 |
|  | 15 | 5 | −26 |
|  | 30 | 6 | −26 |
| 2 | 15 | 6 | −21 |
|  | 30 | 6 | −33 |
| 5 | 60 | 6 | −23 |
| 13 | 7.5 | 6 | −15 |
|  | 15 | 6 | −19 |
|  | 30 | 6 | −24 |
|  | 60 | 6 | −37 |
| 19 | 60 | 6 | −19 |
| 30 | 15 | 5 | −17 |
|  | 30 | 5 | −24 |
|  | 60 | 6 | −34 |
|  | 100 | 5 | −39 |
| 36 | 15 | 6 | −25 |
|  | 30 | 6 | −21 |
|  | 60 | 5 | −27 |
|  | 100 | 5 | −52 |
| 62 | 30 | 6 | −26 |
|  | 60 | 6 | −35 |
| 69 | 15 | 6 | −15 |
|  | 30 | 6 | −28 |
|  | 60 | 6 | −33 |
| 75 | 7.5 | 6 | −26 |
|  | 15 | 6 | −23 |
|  | 30 | 5 | −34 |
| 88 | 7.5 | 6 | −19 |

TABLE 3:

Anti-hypertensive activity (high blood pressure dogs)

| Compound of Example | Dose mg/kg p.o. W | Dose mg/kg p.o. E | n | d* | Maximum change in systolic blood pressure in % (test day) | Significance | Active period (hours) |
|---|---|---|---|---|---|---|---|
| 1 | 10 | 10 | 5 | 5 | −30(2.) | <0.01 | ~5 |
|  | 20 | 20 | 7 | 5 | −33(3.) | <0.01 | >>5 |
| 2 | 50 | 50 | 6 | 3 | −15(3.) | <0.01 | >5 |
| 13 | 20 | 20 | 6 | 5 | −25(3.) | <0.01 | >>5 |
| 62 | 50 | 25 | 5 | 5 | −10 | >0.05 (not significant) | ~3 |
| 75 | 5 | 5 | 5 | 5 | −25(2.) | >0.05 (not significant) | ~5 |
| 88 | 10 | 10 | 6 | 5 | −22(3.) | <0.05 | >5 | d* Test period in days
n Number of test animals

TABLE 4

Compounds of formula (I) $R^1-C=N-O-CH_2-CH-CH_2-N$ with piperidine-X-phenyl(OR^4)(R^5)
                        $\phantom{R^1-C=N}R^2\phantom{-O-CH_2-}R^3$

| Example | $R^1$ | $R^2$ | $R^3$ | X | $R^4O-$ | $R^5$ | Process | Isolated as | melting point (°C.) |
|---|---|---|---|---|---|---|---|---|---|
| 1 | 2-methoxyphenyl | H | OH | N | 2-CH$_3$O— | H | A | 2HCl | 171–173 |
| 2 | phenyl | H | OH | N | 2-CH$_3$O— | H | B | 1HCl<br>oxalate<br>cyclamate | 163–164<br>143–144<br>90–91 |
| 3 | phenyl | H | OH | CH | 2-CH$_3$O— | H | B | 1HCl | 155–157 |
| 4 | phenyl | H | H | N | 2-CH$_3$O— | H | B | 2HCl | 188–189 |
| 5 | phenyl | H | methyl nicotinate | N | 2-CH$_3$O— | H | C | 2HCl | 188–189 |
| 6 | CH$_3$ | H | OH | N | 2-HO— | H | A | 2HCl | 216–217 (decomp.) |
| 7 | (CH$_3$)$_2$CH— | H | OH | N | 2-HO— | H | A | 2HCl | 172–174 (decomp.) |
| 8 | (CH$_3$)$_2$CH— | H | OH | N | 4-HO— | H | A | 2HCl | 158 |
| 9 | (CH$_3$)$_2$CH— | H | OH | N | 2-CH$_3$O— | H | A | 2HCl | 127–128 (decomp.) |
| 10 | HOOC— | H | OH | N | 2-CH$_3$O— | H | A | 2HCl<br>1HCl | 164–165<br>150 (decomp.) |
| 11 | CH$_3$—CH=CH— | H | OH | N | 2-CH$_3$O— | H | A | 2HCl | 143–145 (decomp.) |
| 12 | phenyl-CH=CH— | H | OH | N | 2-CH$_3$O— | H | A | 2HCl | 164–165 (decomp.) |
| 13 | phenyl | H | OH | N | 2-HO— | H | B | 2HCl | 221–223 (decomp.) |
| 14 | phenyl | H | OH | N | 4-HO— | H | B | 2HCl | 223–225 (decomp.) |
| 15 | phenyl | H | OH | N | 2-HO— | 4-HO— | B | 2HCl | 221–222 |

TABLE 4-continued

Compounds of formula (I) $R^1-\underset{\underset{R^2}{|}}{C}=N-O-CH_2-\underset{\underset{R^3}{|}}{CH}-CH_2-N\underbrace{\phantom{XXX}}X\underbrace{\phantom{XXX}}\overset{OR^4}{\underset{R^5}{\phantom{X}}}$

| Example | $R^1$ | $R^2$ | $R^3$ | X | $R^4O—$ | $R^5$ | Process | Isolated as | melting point (0° C.) |
|---|---|---|---|---|---|---|---|---|---|
| 16 | 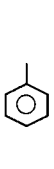 | H | OH | N | 3-CH$_3$O— | H | B | 1HCl | 196–197 |
| 17 | 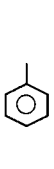 | H | OH | N | 4-CH$_3$O— | H | B | 1HCl | 171–173 |
| 18 | 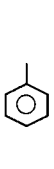 | H | OH | N | 2-CH$_3$O— | 4-Cl— | B | 2HCl | 185–186 |
| 19 | 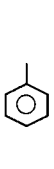 | H | OH | N | 2-CH$_3$O— | 4-CH$_3$O— | B | 2HCl | 198–199 |
| 20 | 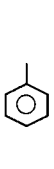 | H | OH | N | 3-CH$_3$O— | 5-CH$_3$O— | B | 1HCl | 167–170 |
| 21 | 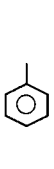 | H | $(CH_3)_3C-\overset{O}{\underset{\phantom{X}}{C}}-O-$ | N | 2-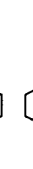 | H | B | 2HCl | 165–166 |
| 22 | 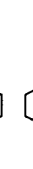 | H | 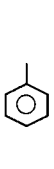 | N | 2-CH$_3$O— | H | C | 2HCl | 197–198 |
| 23 | 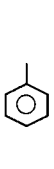 | H | OH | N | 2-CH$_3$O— | H | C | 2HCl | 152–153 |
| 24 | 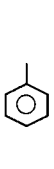 | CH$_3$ | OH | N | 2-CH$_3$O— | H | B | 1HCl | 150–152 |
| 25 | 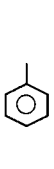 | 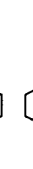 | OH | N | 2-CH$_3$O— | H | B | 2HCl | 154–155 (decomp.) |
| 26 | 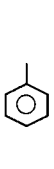 | 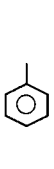 | OH | N | 2-CH$_3$O— | H | B | 1HCl | 201–202 |
| 27 | 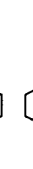 | H | OH | N | 2-CH$_3$O— | H | A | 2HCl | 192–194 |
| 28 | 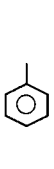 | H | OH | N | 2-CH$_3$O— | H | A | 2HCl | 200–202 |

TABLE 4-continued

Compounds of formula (I) $R^1-\underset{\underset{R^2}{|}}{\overset{\overset{R^3}{|}}{C}}=N-O-CH_2-CH-CH_2-N\underset{}{\overset{}{\bigcirc}}X-\underset{}{\overset{OR^4}{\underset{R^5}{\bigcirc}}}$

| Example | $R^1$ | $R^2$ | $R^3$ | X | $R^4O-$ | $R^5$ | Process | Isolated as | melting point (0° C.) |
|---|---|---|---|---|---|---|---|---|---|
| 29 | 4-CH3-C6H4 | H | OH | N | 2-CH3O— | H | A | 2HCl | 176-177 |
| 30 | 3,5-(CH3)2-C6H3 | H | OH | N | 2-CH3O— | H | A | 2HCl | 181 (decomp.) |
| 31 | 4-(C(CH3)3)-C6H4 | H | OH | N | 2-CH3O— | H | A | 2HCl | 171-173 |
| 32 | 3-CH3O-C6H4 | H | OH | N | 2-HO— | H | A | 2HCl | 190-192 (decomp.) |
| 33 | 3-CH3O-C6H4 | H | OH | N | 4-HO— | H | A | 2HCl | 183-185 (decomp.) |
| 34 | 4-CH3O-C6H4 | H | OH | N | 2-HO— | H | A | Base<br>2HCl | 115-117<br>185-187 (decomp.) |
| 35 | 4-CH3O-C6H4 | H | OH | N | 4-HO— | H | A | Base<br>2HCl | 128-130<br>208-209 (decomp.) |
| 36 | 4-CH3O-C6H4 | H | OH | N | 2-CH3O— | H | A | 2HCl<br>1HCl (Tosylate) | 185-186 (decomp.)<br>194-195 (decomp.) |
| 37 | 3-CH3-C6H4 (OCH3) | H | OH | N | 4-CH3O— | H | A | Base<br>2HCl | ~60<br>65-67 |
| 38 | 2-CH3O-C6H4 (CH3) | H | OH | N | 2-CH3O— | H | A | 2HCl | 176-178<br>168-170 |

TABLE 4-continued

Compounds of formula (I) $R^1-C=N-O-CH_2-CH-CH_2-N$ with $R^2$ and $R^3$ substituents, connected to a piperidine ring bearing a phenyl group with $OR^4$ and $R^5$ substituents.

| Example | $R^1$ | $R^2$ | $R^3$ | $R^4O-$ | X | $R^5$ | Process | Isolated as | melting point (0° C.) |
|---|---|---|---|---|---|---|---|---|---|
| 39 | 4-CH₃O-C₆H₄- | H | OH | 2-C₂H₅O— | N | H | A | 2HCl | 163-164 (decomp.) |
| 40 | 2,4-(CH₃O)₂-C₆H₃- | H | OH | 2-CH₃O— | N | H | A | 2HCl | 153-155 (decomp.) |
| 41 | 2-CH₃O-4-OCH₃ substituted phenyl | H | OH | 2-CH₃O— | N | H | A | 2HCl | 182-184 (decomp.) |
| 42 | 3,4,5-(CH₃O)₃-C₆H₂- | H | OH | 2-HO— | N | H | B | 2HCl | 202-203 |
| 43 | 3,4,5-(CH₃O)₃-C₆H₂- | H | OH | 4-HO— | N | H | B | 2HCl | 202-204 |
| 44 | 3,4,5-(CH₃O)₃-C₆H₂- | H | OH | 2-CH₃O— | N | H | A | Base 1HCl | 93-95 234-236 (decomp.) |
| 45 | CH₃—(CH₂)₂—O—C₆H₄- | H | OH | 2-CH₃O— | N | H | A | 2HCl | 148-150 |
| 46 | CH₃—(CH₂)₃—O—C₆H₄- | H | OH | 2-CH₃O— | N | H | A | 2HCl | 145-147 |
| 47 | C₆H₅—CH₂—O—C₆H₄- | CH₃—CH₂— | OH | 2-CH₃O— | N | H | B | 2HCl | 107-110 |

TABLE 4-continued

Compounds of formula (I) $R^1-C=N-O-CH_2-CH-CH_2-N\underset{}{\overset{}{\diagdown}}X\underset{}{\overset{}{\diagup}}\!\!-\!\!\!\bigcirc\!\!\!-\!\!OR^4, R^5$
with $R^2$ and $R^3$ substituents

| Example | $R^1$ | $R^2$ | $R^3$ | X | $R^4O-$ | $R^5$ | Process | Isolated as | melting point (°C.) |
|---|---|---|---|---|---|---|---|---|---|
| 48 | 3-CF$_3$-C$_6$H$_4$ | H | OH | N | 2-HO— | H | A | 2HCl | 201–203 (decomp.) |
| 49 | 3,5-(CF$_3$)-C$_6$H$_3$ | H | OH | N | 4-HO— | H | A | 2HCl | 204–206 (decomp.) |
| 50 | 3-CF$_3$-C$_6$H$_4$ | H | OH | N | 2-CH$_3$O— | H | A | 2HCl | 192–194 |
| 51 | 4-F-C$_6$H$_4$ | H | OH | N | 2-CH$_3$O— | H | A | 2HCl | 170–172 |
| 52 | 4-Cl-C$_6$H$_4$ | H | OH | N | 2-CH$_3$O— | H | B | 1HCl | 197 |
| 53 | 4-Br-C$_6$H$_4$ | H | OH | N | 2-CH$_3$O— | H | A | 2HCl | 195–197 (decomp.) |
| 54 | 4-Cl-C$_6$H$_4$ | CH$_3$ | OH | N | 2-CH$_3$O— | H | B | 1HCl | 177–178 |
| 55 | 4-NC-C$_6$H$_4$ | H | OH | N | 2-CH$_3$O— | H | A | 2HCl | 176–178 |
| 56 | 2-NO$_2$-C$_6$H$_4$ | H | OH | N | 2-CH$_3$O— | H | A | 2HCl | 175 (decomp.) |
| 57 | 3-NO$_2$-C$_6$H$_4$ | H | OH | N | 2-CH$_3$O— | H | B | 2HCl | 137–138 |
| 58 | H$_3$C-N(CH$_3$)-C$_6$H$_4$ | H | OH | N | 2-CH$_3$O— | H | A | 3HCl | 175 (decomp.) |

TABLE 4-continued

Compounds of formula (I) $R^1-\underset{R^2}{C}=N-O-CH_2-\underset{R^3}{CH}-CH_2-N\diagup X\diagup\text{-}\bigcirc\text{-}OR^4, R^5$

| Example | R¹ | R² | R³ | X | R⁴O— | R⁵ | Process | Isolated as | melting point (° C.) |
|---|---|---|---|---|---|---|---|---|---|
| 59 | 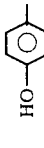 | H | OH | N | 2-CH₃O— | H | A | 1HCl | 205-206 |
| 60 | 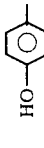 | H | OH | N | 2-HO— | H | A | 2HCl | 203-205 (decomp.) |
| 61 | 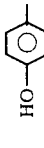 | H | OH | N | 4-HO— | H | A | Base 2HCl | 183-185 210-211 (decomp.) |
| 62 | 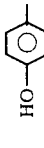 | H | OH | N | 2-CH₃O— | H | A | 2HCl 1HCl | 185-187 173-175 |
| 63 | 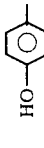 | H | OH | N | 2-C₂H₅O— | H | A | 2HCl | 191-193 |
| 64 | 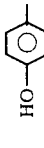 | H | OH | N | 2-CH₃O— | H | A | 2HCl | 175-177 (decomp.) |
| 65 | 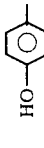 | H | OH | N | 2-CH₃O— | H | A | 2HCl | 193-195 (decomp.) |
| 66 | 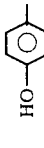 | H | OH | N | 2-CH₃O— | H | A | 2HCl | 143-145 (decomp.) |
| 67 | 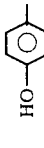 | H | OH | N | 2-HO— | H | A | 2HCl | 208-209 (decomp.) |
| 68 | 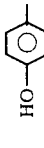 | H | OH | N | 4-HO— | H | A | 2HCl | 215-216 (decomp.) |
| 69 | 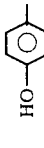 | H | OH | N | 2-CH₃O— | H | A | 2HCl | 188-190 (decomp.) |
| 70 | 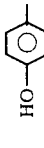 | H | OH | N | 2-CH₃O— | H | A | 2HCl | 202-204 |

TABLE 4-continued

Compounds of formula (I) $R^1-\underset{\underset{R^2}{|}}{C}=N-O-CH_2-\underset{\underset{R^3}{|}}{CH}-CH_2-N\underset{\diagdown}{\diagup}\phantom{X}X\phantom{\diagdown}$—⟨aryl⟩—$OR^4$, $R^5$

| Example | $R^1$ | $R^2$ | $R^3$ | X | $R^4O-$ | $R^5$ | Process | Isolated as | melting point (°C.) |
|---|---|---|---|---|---|---|---|---|---|
| 71 | (piperazine-CH₂-C(OH)(CH₂O-)- with 2-methoxycyclohexyl) | H | OH | N | 2-CH₃O— | H | A | 4HCl | 192–193 (decomp.) |
| 72 | 3-pyridyl (4-methyl) | H | OH | N | 2-CH₃O— | H | A | 3HCl × 1H₂O / 1HCl | 178 (decomp.) / 169–170 (decomp.) |
| 73 | 3-pyridyl | H | OH | N | 2-HO— | H | A | 3HCl | 215–217 (decomp.) |
| 74 | 3-pyridyl | H | OH | N | 4-HO— | H | A | Base / 3HCl | 185–186 / 225–226 (decomp.) |
| 75 | 4-pyridyl | H | OH | N | 2-CH₃O— | H | A | 3HCl × 1H₂O / 2HCl | 174 (decomp.) / 198–199 (decomp.) |
| 76 | 3-pyridyl | H | OH | N | 2-CH₃O— | H | A | 1HCl / 3HCl × 1H₂O | 110–112 / 165 (decomp.) |
| 77 | 3-pyridyl | phenyl | OH | N | 2-CH₃O— | H | B | 3HCl | 155–158 (decomp.) |
| 78 | 3-pyridyl | phenyl | OH | N | 2-CH₃O— | H | B | 3HCl | 150–153 |

TABLE 4-continued

Compounds of formula (I) $R^1-\underset{\underset{R^2}{|}}{C}=N-O-CH_2-\underset{\underset{R^3}{|}}{CH}-CH_2-N\begin{pmatrix}X\\ \end{pmatrix}\begin{pmatrix}\phantom{x}\\ \end{pmatrix}\begin{matrix}OR^4\\R^5\end{matrix}$

| Example | R¹ | R² | R³ | X | R⁴O— | R⁵ | Process | Isolated as | melting point (0° C.) |
|---|---|---|---|---|---|---|---|---|---|
| 79 | 4-pyridyl | phenyl | OH | N | 2-CH₃O— | H | B | 3HCl | 142–145 |
| 80 | 2-methylindol-3-yl | H | OH | N | 2-CH₃O— | H | A | 2HCl | 170–172 |
| 81 | 5-methoxy-2-methylindol-3-yl | H | OH | N | 2-CH₃O— | H | A | 1HCl | 160–162 (decomp.) |
| 82 | 5-chloro-1,4-dimethylimidazol-... | phenyl | OH | N | 2-CH₃O— | H | B | 3HCl | 146–148 |
| 83 | 5-methylamino-1,4-dimethylimidazol-... | phenyl | OH | N | 2-CH₃O— | H | B | 3HCl | 175–177 |
| 84 | 5-dimethylamino-1,4-dimethylimidazol-... | phenyl | OH | N | 2-CH₃O— | H | B | 3HCl | 157–160 |

TABLE 4-continued

Compounds of formula (I) R¹—C=N—O—CH₂—CH—CH₂—N(piperidine/piperazine)—X—(phenyl with OR⁴ and R⁵)
                                    |              |
                                    R²             R³

| Example | R¹ | R² | R³ | X | R⁴O— | R⁵ | Process | Isolated as | melting point (° C.) |
|---|---|---|---|---|---|---|---|---|---|
| 85 | (1-isopropyl-imidazol-2-yl)-CH(CH₃)-phenyl | H | OH | N | 2-HO— | H | A | 3HCl | ab 152 (decomp.) |
| 86 | (1-isopropyl-imidazol-2-yl)-CH(CH₃)-phenyl | H | OH | N | 4-HO— | H | A | 2HCl | 195 (decomp.) |
| 87 | (1-isopropyl-imidazol-2-yl)-CH(CH₃)-phenyl | H | OH | N | 2-CH₃O— | H | A | 3HCl | 208–210 (decomp.) |
| 88 | (1-isopropyl-imidazol-2-yl)-CH(CH₃)-phenyl | H | OH | N | 2-CH₃O— | H | A | 3HCl | 193-195 (decomp.) |
| 89 | 8-cyano-1,3,7-trimethylxanthine | H | OH | N | 2-CH₃O— | H | A | 2HCl | 224-226 |

TABLE 4-continued

Compounds of formula (I) $R^1-C=N-O-CH_2-CH-CH_2-N\underset{\phantom{x}}{\overset{\phantom{x}}{\diagdown}}\phantom{x}X\phantom{x}\diagup\phantom{x}$ with $R^2$ on C and $R^3$ on middle CH, ending in piperazine-phenyl with $OR^4$ and $R^5$

| Example | $R^1$ | $R^2$ | $R^3$ | X | $R^4O-$ | $R^5$ | Process | Isolated as | melting point (0° C.) |
|---|---|---|---|---|---|---|---|---|---|
| 90 | (3-methylthiophen-2-yl) | H | OH | N | 2-$CH_3O-$ | H | A | 2HCl | 166–168 |
| 97 | (2,2'-dimethylbiphenyl) | H | OH | N | 2-$CH_3O-$ | H | B | 2HCl | 180–183 (decomp.) |
| 98 | (3-methoxyphenyl with $OCH_3$) | H | H | N | 2-$CH_3O-$ | H | B | 2HCl | 169–171 |

It is not intended that the examples given herein should be construed to limit the invention thereto, but rather they are submitted to illustrate some of the specific embodiments of the invention. Resort may be had to various modifications and variations of the present invention without departing from the spirit of the discovery or the scope of the appended claims.

What we claim is:

1. A compound of the formula I

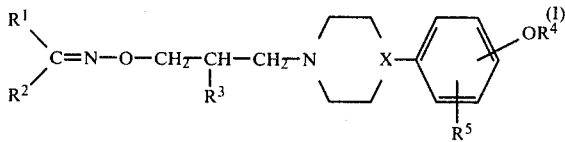

and the physiologically acceptable salts thereof wherein $R^1$ represents pyridyl; imidazolyl substituted by alkyl or phenylalkyl, each having up to two carbon atoms in the alkyl moiety; indolyl; 5-methoxy-indolyl; chromonyl; naphthyl; phenyl or phenyl substituted by from 1 to 3 substituents selected from the group consisting of alkyl and alkoxy each having up to 6 carbon atoms, haloalkyl with up to 2 carbon atoms, halogen, cyano, nitro, hydroxy and amino, which amino may be substituted by one or two alkyl groups each having up to 2 carbon atoms, and a methylenedioxy group;

$R^2$ represents hydrogen;

$R^3$ represents hydroxy;

$R^4$ represents a member of the group consisting of hydrogen, methyl and ethyl, the radical $OR^4$ being in 2 or 4 position;

$R^5$ represents hydrogen, halogen, alkoxy having up to two carbon atoms or hydroxy and X represents nitrogen.

2. A compound as claimed in claim 1 of the formula

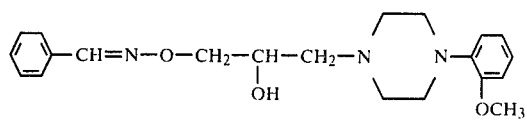

and the physiologically acceptable salts thereof.

3. A compound as claimed in claim 1 of the formula

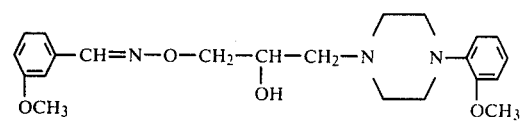

and the physiologically acceptable salts thereof.

4. A compound as claimed in claim 1 of the formula

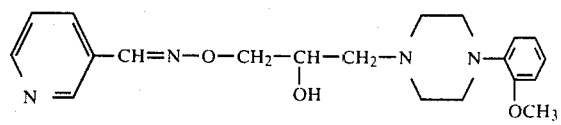

and the physiologically acceptable salts thereof.

5. A pharmaceutical composition for the treatment of hypertonic conditions comprising a compound as defined in claim 1 in combination with a pharmaceutical carrier or excipient.

6. A composition as claimed in claim 5 containing a compound as claimed in claim 1 in an amount of from 1 to 10 mg/dosage unit.

* * * * *

UNITED STATES PATENT AND TRADEMARK OFFICE
CERTIFICATE OF CORRECTION

PATENT NO. : 4,328,227
DATED : May 4, 1982
INVENTOR(S) : Ulrich Gebert, et al

It is certified that error appears in the above-identified patent and that said Letters Patent are hereby corrected as shown below:

The first name of the first-named inventor is "Ulrich".

Item [75] of the cover page should read "Ulrich Gebert" and not --Gebert Ulrich--.

Signed and Sealed this

Twenty-first Day of September 1982

[SEAL]

Attest:

*Attesting Officer*

GERALD J. MOSSINGHOFF

Commissioner of Patents and Trademarks